United States Patent [19]

McCormick

[11] Patent Number: 4,923,978

[45] Date of Patent: May 8, 1990

[54] PROCESS FOR PURIFYING NUCLEIC ACIDS

[75] Inventor: Randy M. McCormick, Wilmington, Del.

[73] Assignee: E. I. Du Pont de Nemours & Company, Wilmington, Del.

[21] Appl. No.: 138,038

[22] Filed: Dec. 28, 1987

[51] Int. Cl.$^5$ .................. C07H 21/00; C07K 3/18; C07K 3/20

[52] U.S. Cl. ........................ 536/27; 536/28; 536/29; 530/415; 530/417; 530/821

[58] Field of Search ................ 536/27, 28, 29, 127

[56] References Cited

PUBLICATIONS

Guenther et al, Chem. Abstr., 107; 192006d (1987).
Bio-Rad Price List, Jan., 1986, Richmond, CA, p. 30, Column 2.
Hillan et al (I), Chem. Abstr., 104;83889m (1986).
Hillan et al. (II), Chem Abstr., 104; 83890n (1986).
Rainin Instrument Co. Catalog, Woburn, Mass., 1985, p. 15, Column 2.
Edwardson et al., Chem. Abstr., 104; 84658x (1986).
Kirby, Biochem. J., vol. 66, 494–504 (1957).
Marmur, J. Mol. Biol., vol. 3, 208–218 (1961).
Thomas et al., *Analytical Biochemistry*, 93; 158–166 (1979).
Vogelstein et al., *Proc. Natl. Acad. Sci. USA*, 26 (2):615–619 (1979).
Kirkland, *J. Chromatographic Sci.*, 9: 206–214 (1971).
Kohler et al., *J. Chromatography*, 385:125–150 (1987).
Watanabe et al., *J. Solid-Phase Biochem.*, 3: 161–173 (1978).
Brawerman, "The Isolation of RNA from Mammalian Cells", Methods in Cell Biology, 7:1–22 (1973).

*Primary Examiner*—Ronald W. Griffin
*Assistant Examiner*—L. Eric Crane
*Attorney, Agent, or Firm*—William H. Hamby

[57] ABSTRACT

The process for separating the proteinaceous materials from nucleic acids involves contacting a solution containing the proteinaceous materials and nucleic acids with a solid phase extraction material capable of binding proteins to form bound and unbound fractions and then isolating the unbound fraction containing the nucleic acids.

4 Claims, No Drawings

PROCESS FOR PURIFYING NUCLEIC ACIDS

BACKGROUND OF THE INVENTION

1. Field of the Invention

This invention relates to a method for using solid phase extraction materials to purify nucleic acid samples contaminated with proteinaceous material.

2. Background

T. Maniatis, et al. [Molecular Cloning - A Laboratory Manual, (New York: Cold Spring Harbor Laboratory, 1982), pp 458-460] describe a method of purifying nucleic acids based on the procedures described by K. S. Kirby [Biochim. J., Vol. 66, 494-504 (1957)] and J. Marmur [J. Mol. Biol , Vol. 3, 208-218 (1961)]. This method uses phenol in a liquid/liquid extraction procedure, whereby the protein contaminating an aqueous nucleic acid sample is extracted into the phenol phase, leaving the nucleic acid in the aqueous phase. This nucleic acid purification procedure may actually involve a series of liquid/liquid extractions, in which an aqueous volume of nucleic acid sample is sequentially extracted with equal volumes of liquified phenol, phenol/chloroform/isoamyl alcohol (50/48/2), and chloroform/isoamyl alcohol (96/4). After each extraction, the organic phase containing protein (and some nucleic acid) is back-extracted with an aqueous buffer to recover any nucleic acid extracted into the organic phase. The aqueous nucleic acid sample must then be exhaustively extracted with diethyl ether to remove any residual phenol, chloroform, or isoamyl alcohol. Finally, the residual diethyl ether is removed either under reduced pressure or by blowing nitrogen over the sample for ten minutes. Removal of the residual organic solvents is of paramount importance, as they would otherwise interfere in subsequent cloning or hybridization procedures in which the nucleic acid might be used.

Although phenol extraction is a very effective method for the purification of nucleic acid samples and is very widely used, the procedure is also labor-intensive and time-consuming. Other disadvantages of this technique include the hazards (chemical irritant, carcinogen, stench and flammability) associated with the use of the organic solvents (phenol, chloroform, isoamyl alcohol and diethyl ether).

A second method of nucleic acid purification is based on the preferential adsorption of nucleic acids using NENSORB 20 TM Nucleic Acid Purification Cartridges (DuPont). A proteinaceous DNA sample is passed through a column of NENSORB TM particles, binding the DNA to the particles, and allowing most of the proteinaceous material to be washed from the column with an aqueous buffer. The bound nucleic acid is then desorbed from the particles by passing 20% aqueous ethyl alcohol (or 50% aqueous methyl alcohol) through the column and the DNA is collected in the column effluent Prior to use of the DNA in cloning or hybridization, the alcohol must be removed from the DNA solution by pulling a vacuum on the sample for several hours.

The use of NENSORB TM has other limitations The NENSORB TM material, besides binding nucleic acid, also binds protein to a variable extent This not only limits the capacity for quantitatively binding nucleic acid from a sample heavily contaminated with proteinaceous material (e.g., blood serum, tissue homogenate), it also affords the possibility that some loosely bound protein may elute with the nucleic acid when the latter is desorbed from the NENSORB TM by the use of aqueous alcohol. Three different solvents are needed to activate the NENSORB TM column, wash the unbound protein from the column, and then elute the nucleic acid from the column. Nucleic acid is eluted from the column in a solvent (20% ethyl alcohol or 50% methyl alcohol) that is incompatible in protocols of subsequent uses of the nucleic acid (e.g., cloning, hybridization assays, etc.). The purification procedure using NENSORB TM can be time-consuming, requiring an hour or more to purify a single sample of nucleic acid.

C. A. Thomas et al., Analytical Biochemistry, Vol. 93, 158-166 (1979), disclose the use of glass fiber filters to adsorb protein and protein-DNA complexes from aqueous DNA samples. This method suffers from the following disadvantages: (1) The aqueous sample of DNA must contain at least 300 mM NaCl for the protein to bind effectively to the glass fiber filter. This relatively high salt concentration would have to be lowered by removing the salt from the DNA sample (or diluting the solution) prior to further use of the DNA in biological reactions, such as digesting the DNA with a restriction enzyme. (2) The recovery of DNA from the filter is high only if the filter is extensively washed with an aqueous buffer. (3) The low specific surface area (approx. 2 m$^2$/g) of the glass fibers results in a low protein-binding capacity of the glass fiber filter. The maximum protein-binding capacity is estimated to be 8.5 mg of bovine serum albumin (B$A) per gram of glass fiber filter.

B. Vogelstein et al., Proc. Natl. Acad. Sci. U.S.A., Vol. 26, No. 2, 615-619 (1979), disclose a method for separating DNA from agarose by binding the DNA to glass, preferably glass powder, in the presence of NaI. The DNA was removed from the glass by elution with Tris·HCl, pH7.2/0.2M NaCl/2 mM EDTA. It is also disclosed that silica gel and porous glass beads are unsuitable for DNA purification.

J. Kirkland, J. Chromatographic Sci., Vol. 9, 206-214 (1971), discloses the preparation of surface-modified silica gels by reacting silane reagents with the surface of the porous shell of Zipax TM controlled-surface chromatographic support.

J. Kohler, et al., J. Chromatography, Vol. 385, 125-150 1(1987), disclose the preparation of fully hydroxylated calcined silica by the dissolution and redeposition of silicic acid.

T. Watanabe et al., J. Solid-Phase Biochem., Vol. 3, 161-173 (1978), discloses the preparation of immobilized tannins for protein adsorption.

The object of this invention is to provide an improved solid-phase extraction procedure for removing proteinaceous contaminants for nucleic acid samples. The method should be capable of removing large proportions of proteins from minute quantities of nucleic acid and recovering the latter in a biologically active state. The method should also be rapid, convenient, provide quantitative recovery of the nucleic acid and minimize the use of hazardous materials. It should also not introduce contaminants or impurities into the nucleic acid sample that may interfere in subsequent uses of the nucleic acid.

SUMMARY OF THE INVENTION

The process for separating the proteinaceous materials from nucleic acids involves contacting a solution containing the proteinaceous materials and nucleic acids with a solid phase extraction material capable of binding proteins to form bound and unbound fractions and then isolating the unbound fraction containing the nucleic acids.

DETAILED DESCRIPTION OF THE INVENTION

The solid phase extraction materials which are useful in the claimed process for the separation of proteins and nucleic acids are particulate solid materials with very high affinities for proteinaceous materials and very low affinities for nucleic acids. The solid phase extraction materials are characterized by having large specific surface areas with high concentrations of mildly acidic surface hydroxyl groups and low surface concentrations of polyvalent cationic species.

Solid phase extraction materials with large specific surface areas are preferred due to their capacity to remove large amounts of proteins. Preferably, the specific surface area of the extraction material is at least 50 m$^2$/g; more preferably, it is at least 100 m$^2$/g. These high surface areas are due to the presence of pores throughout the particulate material. The pores should be $>60$ Å effective diameter and, though there is no upper limit on the pore diameter, a reasonable limit of 500 Å is preferred in order to maintain a high specific area. The preferred range is 60 Å to 50 Å.

High concentrations of mildly acidic hydroxyl groups on the extraction material serve both to increase the affinity of the extraction material for proteinaceous compounds and to decrease its affinity for polyanions such as nucleic acids. The minimum effective concentration of mildly acidic hydroxyl groups is 0.1 $\mu$mole/m$^2$. Preferably, the concentration of mildly acidic hydroxyl groups is 1-8 $\mu$mole/m$^2$; more preferably, it is 8 $\mu$mole/m$^2$.

Preferably, the pK$_a$ of the surface hydroxyl groups is between 6 and 10.

The concentration of polyvalent cationic species on the surface of the solid phase extraction material should be minimized to prevent the complexation of anionic nucleic acids by cationic surface species. Trivalent metals such as iron and aluminum are particularly deleterious to the performance of the extraction materials.

Solid phase extraction materials with the desirable properties discussed above may be prepared in a number of ways, using either a homogeneous particulate material or a core particulate material on whose surface the desired functional moieties are introduced via chemical reactions. For the former case, rehydrated silica gel has been found to possess the desired properties. Silica gel intrinsically possesses a large surface population (8 $\mu$mole/m$^2$) of mildly acidic ($6<$pK$_a<10$) hydroxyl groups and thus meets the primary requirements above. It is also very effective at adsorbing proteinaceous material. However, the surface of the silica gel must be freed of polyvalent cationic species if nucleic acids are to be prevented from being adsorbed on the surface of the silica particles. This can be achieved is several ways.

The preferred method involves the rehydroxylation and purification of the surface layer of the silica particle by dissolution and reprecipitation of the surface layer of the particles according to Kohler et al., J. Chromatography, Vol. 385, 125–150 (1987). In this procedure, the outer surface of the silica particles is dissolved in a dilute solution of hydrofluoric acid at an elevated temperature. The dissolved silica is then reprecipitated onto the surface of each particle by allowing the solution containing the dissolved silica to cool to room temperature where it has a lower solubility in aqueous media. As the layer reprecipitates, contaminants present in the outer layer of silica which had been dissolved remain in the solution and an essentially pure layer of silica is formed around the core particle.

Alternatively, polyvalent metallic contaminants may be leached from the silica by treating it sequentially with moderately concentrated hydrochloric and nitric acids at elevated temperatures. This process solubilized and extracts metallic impurities on the surface of the silica gel particles, leaving a surface which is essentially pure silica.

A third method of preparing the solid phase extraction material is to polymerize a thick layer of organic material containing a large population of mildly acidic hydroxyl groups around the surface of a porous support material. This can be done by allowing an organic silane containing the desired chemical functionality to react with silica, where the silane will cross-link with itself and with the silica particles to form a thick immobilized layer of organic polymer [J. Kirkland, et al., J. Chromatographic Sci., Vol 9, 206–214 (1971)] containing the desired population of mildly acidic hydroxyl groups. Whereas the hydroxyl groups impart the surface with the ability to adsorb large quantities of proteinaceous material, they also shield the nucleic acids from any polyvalent cationic species in the core particle below the layer of organic polymer and thus prevent nucleic acids from binding to the solid phase extraction material. Numerous organic silanes could be used for this reaction. For example, use of silanes to immobilize phenol (pK$_a$=9.9), beta-napthol (pK$_a$9.6) or tannin (polyhydroxycarboxylic acids) onto the surface of support particles would provide useful solid phase extraction materials. Useful support materials may include silica, cellulose, agarose and other materials which possess a large population of active surface groups.

By whatever method of preparation of the solid phase extraction material, at least two protocols can be implemented for its use in removing proteinaceous contamination from samples of nucleic acids. According to the first protocol, a quantity of the particulate solid phase extraction material is added to a volume of sample that is to be deproteinized. The mixture is gently agitated to keep the particulate material in suspension. Because of the small size and large surface area of the solid phase extraction material, diffusion and adsorption of the proteinaceous material to the solid phase extraction material is rapid (on the order of minutes). The particulate material containing the adsorbed protein is then separated from the aqueous nucleic acid sample by any convenient means, e.g., centrifugation or filtration. This protocol is most effective when a large volume ($>1$ mL) of sample contains small quantities of protein and thus only a small quantity of particles (e.g., $<10$ mg) is required for quantitative removal of the protein.

In a second protocol, the solid phase extraction material is packed into a column and the aqueous sample is passed through the column. To accomplish this, a quantity of particles is weighed into a spin column and packed by tapping the sealed end of the column onto the bench top. The column may also be spun at high speed in a centrifuge; the centrifugal force packs the particles tightly in the bottom of the column. The column is then wetted by pipetting a volume of the appropriate buffer (a volume at least equal to the volume of particles in the column) onto the column and the buffer is then allowed to seep down into the bed of the column.

The excess buffer is then removed from the column bed by spinning the column at high speed in a centrifuge for about 30 sec. Any buffer eluted from the column bed is discarded. The column is now ready to accept the sample of nucleic acid which is to be deproteinized; the sample is pipetted onto the head of the column and allowed to seep down into the bed of the column, where the proteinaceous material binds to the particles and the nucleic acids remain in solution. The column is next spun at high speed in a centrifuge to elute the aqueous phase containing the nucleic acids into a collection tube. Recovery of nucleic acid from the column is typically >80% of the quantity applied to the column. The recovery can by improved to about 95% if a small volume (typically $\frac{1}{3}$ to $\frac{1}{2}$ the volume of sample originally applied to the column) of the appropriate buffer is pipetted onto the head of the column and spun through at high speed in the centrifuge. This washes any trapped nucleic acid through the column bed and this wash should be added to the column effluent containing the bulk of the nucleic acid. This protocol works best for samples that are heavily contaminated with proteinaceous material, when it is necessary to use a large quantity of particles (relative to the volume of the sample). Also, this protocol is useful when a very small volume of sample (e.g., 50 μL) must be deproteinized and implementing the preceding method would be cumbersome.

Several constraints can be placed on the nature of the buffers employed in the column wetting step and in the column wash step as outlined previously. The chemical nature of the buffer does not appear to be significant, though the use of salts of polyvalent metal cations (e.g., Al, Fe, Ti, etc.) should be avoided. Standard biochemical buffers such as TE (10 mM Tris·HCl, 1 mM EDTA, pH 6.75), STE (10 mM Tris·HCl, 100 mM NaCl, 1 mM EDTA pH 7.0) or PBS (120 mM NaCl, 2.7 mM KCl, 10 mM phosphate pH 7.4) work very well. Generally, the pH of the buffer should be in the range of 6 to 7.5; at lower pH values, nucleic acid may bind to the solid phase extraction material, resulting in reduced recoveries, whereas at high pH values, the support may dissolve since silica gel has a significant solubility in alkaline solutions. By the same token, if the sample of nucleic acid has a pH outside of the above range, it must be neutralized to a pH of 6 to 7.5 prior to applying it to the column for removal of proteins. The preferred pH range for all buffers and samples would be in the range of 6.5 to 7.0.

The diameter of the pores of the solid phase extraction material should be large enough to allow entry of proteins so they may be adsorbed onto the surface of the internal pores. This will maximize the capacity of the support for removing protein from samples. Pores must also be large enough to prevent nucleic acid from becoming trapped in the pore volume. It has been found that minimum pore diameters somewhere 60 and 150 Å provide the required characteristics. There is no critical upper limit on the pore diameter, though as the pore diameter of the particle increases, the specific surface area decreases. Thus, a reasonable upper limit of 300 to 500 Å can be defined. Particles with pore diameters larger than this limit have reduced surface area and, consequently, reduced protein binding capacity.

The solid phase extraction material is useful for removing proteinaceous contaminants from a wide range of nucleic acid samples. Demonstrated uses include removal of enzymes from restriction digests, removal of alkaline phosphatase from dephosphorylation reaction mixtures and removal of kinase enzymes from labeling reaction mixtures. It is anticipated that other common enzymes such as reverse transcriptase, DNA polymerase, DNA ligase, and terminal transferase, which are commonly used in molecular biology, could also be removed from nucleic acid samples under the appropriate experimental conditions.

In addition, the solid phase extraction material has utility for the isolation and purification of nucleic acids from numerous biological samples. The material has been demonstrated for purification of DNA from organisms in samples of whole blood; it is anticipated that similar isolations from other samples of clinical interest, such as sputum, urine, feces, and tissue would be possible once the appropriate purification protocol has been developed. Such purified nucleic acid samples should be directly usable in clinical hybridization assays. Furthermore, the solid phase extraction material should have utility for the isolation and purification of nucleic acids from organisms grown in culture media expressly for the purpose of producing DNA for cloning purposes or other genetic engineering uses.

The solid phase extraction material is useful for removing proteinaceous impurities from a wide range of nucleic acids. For example, the material can be used to remove kinase enzymes which are used in the radiolabeling of mononucleotides such as dATP, dCTP, etc. The material has also been used to remove alkaline phosphatase from a mixture of DNA ranging from 125 base pairs (bp) to 21,226 bp. The material has been used extensively with pBR322 DNA (4362 bp). In addition, the material has been used with intact lambda DNA (49,000 bp) and no degradation of this DNA by mechanical shearing was observed. Larger strands of DNA may be susceptible to degradation by shear forces as they pass through the column of solid phase extraction material, though this is not known with certainty. This problem could be minimized by using a larger particle size for producing the solid phase extraction material, thereby reducing shear forces in columns packed with such particles.

The process of this invention for the deproteinization of samples containing nucleic acids has the following advantages over currently used methods:

1. Because the solid phase extraction material is essentially insoluble in appropriate aqueous buffers, it will not dissolve in the nucleic acid sample and thus subsequent procedures (e.g., extractions) to remove it are not needed as in the phenol/chloroform extractions.

2. The nucleic acid is eluted in an aqueous medium that is essentially identical (except for the removal of proteins) to the medium in which it was applied to the column. Thus, the nucleic acid is in a solvent that is compatible with subsequent biological procedures in which it is used. No contaminants (i.e., phenol, chloroform, ethanol, etc.) are present to inhibit or deactivate enzymes used in subsequent biological procedures.

3. The purification protocol using this material requires 5 to 10 min to execute for one sample, whereas procedures based on phenol/chloroform extractions or NENSORB ™ can require one hour or more. In addition, processing additional samples requires two min per sample.

4. No special reagents are required to perform this procedure. TE (pH 6.75) is an acceptable buffer for wetting and washing the column and this buffer is available in all labs which work with nucleic acids. In addition, the need for toxic or dangerous reagents is obviated.

5. Recovery of nucleic acids, is high, typically 80–95%.

6. Unlike purification methods based on adsorption of DNA to a support, this method does not shear large fragments of DNA. Thus, the integrity of the sample is maintained. Shearing of DNA is possible in methods based on adsorption of the nucleic acid to a solid phase material because with long fragments of DNA (e.g., 10 kilobase pairs or more), the two ends of the strand of DNA may be adsorbed to two different particles simultaneously and when agitated, the two particles move in different directions and pull the strand of DNA into two smaller fragments. Since in the procedure of this invention, the DNA is not adsorbed to the solid phase (the protein is instead), this degradation of the DNA is not possible.

The following examples are intended to illustrate the invention.

EXAMPLES

General Methods and Reagents.

pBR322 DNA and PST restriction enzyme were obtained from Pharmacia, Inc., Piscataway, N.J. 10 x PST restriction digestion buffer contains 500 mM NaCl, 100 mM Tris HCl pH 7.5, 100 mM MgCl$_2$ and 10 mM dithiothreitol. Calf intestinal alkaline phosphatase was obtained from Boehringer Mannheim Biochemical, Indianapolis, Ind. BCIP (5-bromo-4-chloro-3-indolyl phosphate) was obtained from Bethesda Research Labs, Gaithersburg, Md.

Example 1

Preparation and Use of Silane-Treated Silica Gel

A. Preparation of the Silica Support.

Fractosil 500 (20.5 g, E. Merck, Darmstadt, W. Germany) was washed with three 100 mL aliquots of 25% (v/v) nitric acid at room temperature by suspending the silica particles for 10 min in the aqueous acid and then decanting the excess acid once the particles had settled to the bottom of the beaker. The acid-treated particles were exhaustively rinsed with distilled, deionized water until the supernatant had attained a pH of 5.5. The particles were then transferred to a Buchner funnel fitted with medium porosity filter paper, rinsed with high purity methanol (3×100 mL) and dried for 1 h at 80° C. (630 mm Hg).

B. Polymerization of Aminophenyltrimethoxysilane onto the Silica Support.

Aminophenyltrimethyoxysilane (4.0 mL, Petrarch Systems, Inc., Bristol, Pa.) was added to distilled, deionized water (24 mL) and isopropyl alcohol (12 mL) in a round-bottom flask fitted with a reflux condenser and a magnetic stirbar. The resulting mixture was stirred until the silane was completely dissolved. Acid-washed silica particles (6.1 g) were added to the silane solution and the mixture was refluxed for 2 h at 81° C. Glacial acetic acid (3.5 mL) was added to the flask and the mixture was refluxed for an additional hour. The suspension was allowed to cool to room temperature, after which time the silica particles had settled to the bottom of the flask. The black supernatant was decanted and the particles were exhaustively washed with high-quality methanol until the wash liquid was colorless. The aminophenyl-derivatized silica particles were then collected on a Buchner funnel and air was pulled through the particle bed to remove residual alcohol. The particles were further dried under a medium intensity lamp. Carbon and nitrogen analysis of the particles indicated a thick layer of carbonaceous material had been polymerized onto the surface of the silica particles (6.27% C., 1.13% N).

C. Diazotization of the Silane-Treated Support

The aminophenyl-derivatized silica gel (6.90 g) was added to an ice-cold solution of water (10.0 mL) and concentrated sulfuric acid (7.0 g), and the particles suspended in this solution by magnetic stirring. Finely crushed ice (approx. 17 g) was added to the above mixture and then a solution of sodium nitrite (2.24 g) in water (5.33 dropwise over a period of 8–10 min. The temperature of the mixture was maintained between 0°–5° C. during this time. The particles were allowed to settle and then the supernatant was decanted from the mixture. The particles were then washed three times by suspending them in 100 mL of cold water, allowing the particles to settle, and decanting the supernatant. The resulting particles, in which the surface amines have been converted to the corresponding diazonium salts, were used in the hydrolysis reaction described below.

D. Hydrolysis of the Diazonium Salt

Concentrated sulfuric acid (32 mL) was added to water (24 mL) and this mixture was heated to boiling (approx. 160° C.). The diazonium salt-containing particles were added slowly to the hot acid while maintaining boiling with a subdued effervescence from the nitrogen gas evolved from the decomposition of the diazonium salt. The mixture was boiled for approximately 5 min, and then placed in an ice bath to speed cooling. The acidic supernatant was decanted from the particles which were then washed with distilled, deionized water (5×200 mL). The particles were collected on a Buchner funnel fitted with medium porosity filter paper and rinsed with methanol (200 mL). Air was pulled through the particle bed to remove residual methanol and the particles were dried under a medium intensity infrared lamp. Elemental analysis revealed that the particles contained 0.55% carbon and less than 0.01% nitrogen by weight.

E. Removal of Protein Using Silane-Treated Silica Gel

The silane-treated silica gel described in part D above was tested for its effectiveness in removing a model protein (bovine serum albumin, BSA) from solution, as well as for its lack of binding to DNA (salmon sperm DNA). Aliquots of BSA were placed in various phosphate buffers (pH=5.0–7.0), the samples mixed with 250 mg of silane-treated silica gel and then the solutions separated from the silica gel by pelletizing the silica particles in a centrifuge. The initial buffered protein solution and the filtrate were analyzed by uv absorbance (200–480 nm). Comparison of the uv spectra showed that protein removal was always >90%. Similar testing using aliquots of salmon sperm DNA showed that DNA recovery was always >85%.

Example 2

Nucleic Acid Purification Using Hydrofluoric Acid-Treated Silica Gel

A. Preparation of Rehydrated Silica Gel.

Silica gel (140 g, PSM300 Zorbax, lot 9, Du Pont) was heated in a quartz crucible at 975° C. for 2 h in a muffle furnace, and then 15 g of the cooled silica gel was placed in a round bottom flask fitted with a reflux condenser. Distilled, deionized water (150 mL) containing 75 ppm HF was added to the flask and the mixture was refluxed at 110° C. for 72 h. The mixture was allowed to cool to room temperature, and then the silica gel was washed with 1 L of distilled, deionized water. The silica gel was boiled overnight in water (150 mL), washed sequentially with water (500 mL) and acetone (300 mL), and finally dried at 110° C. for 5 h.

B. Use of Rehydrated Silica Gel.

To Tube A were added 1 μg (15 μL) of pBR322 DNA, 32 units (12 μL) of PST restrictive enzyme, 6 μL of 10 x PST restrictive digestion buffer (a low strength restrictive buffer) and 37 μL of water. The contents of this tube were mixed and incubated at 37° C. for 1.25 h. To Tube B were added reagents identical to those in Tube A. However, immediately after mixing, the contents of this tube were pipetted onto the head of a spin column containing 60 mg of hydrofluoric acid-treated silica gel. The column had been packed and wetted with 1 x PST restriction buffer immediately prior to adding the sample. The sample was allowed to seep down into the column bed and the column was spun for 5 min in an Eppendorf centrifuge (Model 5412) and the effluent was collected. An aliquot of the column effluent was removed to a third reaction tube (Tube C) and 1 μL (16 units) of PST restriction enzyme was added The contents of this tube were mixed and incubated for 1 25 h at 37° C. Aliquots of Tubes A–C were then mixed with agarose gel-loading buffer (0.25% bromophenol blue, 0.25% xylene cyanol, and 30% glycerol in water), and a portion of each was applied to a 0.7% agarose electrophoresis gel (0.105 g agarose, 14.8 mL TBE buffer containing 0.5 μg/mL ethidium bromide) in a BioRad Mini-Cell Submarine Electrophoresis Device The gel was run at 100V applied potential for about 4 h in a 0.5X TBE Buffer (0.5X TBE=0.0445M tris-borate, 0.0445M boric acid, 0.001 M EDTA, pH 8 0). Photographs of the gel were taken via transillumination with 254 nm UV light.

A linearized DNA fragment of length equal to a linearized pBR322 standard was obtained from Tube A, indicating that the PST restriction enzyme cut the circular pBR322 in one place. The DNA from Tube B ran as circular DNA; no DNA band was observed at the position on the gel corresponding to linearized pBR322, indicating that the DNA had not been cut by the enzyme, i.e., the enzyme had been removed by passage through the column. A linearized DNA fragment of length equal to a linearized pBR322 standard was also obtained from Tube C, indicating that the DNA could be cut by the restriction enzyme and that passing the DNA through the column did not alter the DNAs biological activity or remove any of the necessary buffer components (e.g., $MgCl_2$); it removed only the PST restriction enzyme.

This Example demonstrates that passage of a sample which contains DNA and proteins through a spin column containing rehydrated silica gel effectively removes those proteins, e.g. PST restriction enzyme, from the sample. It also indicates that the DNA collected in the effluent from the column is biologically active and that the column does not add impurities to the DNA that would inhibit enzymes used to modify the DNA in subsequent biological reactions.

Example 3

Removal of Eco RI Restriction Enzyme

The procedure described in Example 2 was repeated using Eco RI restriction enzyme and buffer (a medium strength buffer) in place of the PST restriction enzyme and buffer. Only circular pBR322 DNA was observed in the column effluent from tube B, indicating that passage of the mixture through the column had removed all of the Eco RI restriction enzyme before it could cut the DNA. .

Example 4

Removal of Sal I Restriction Enzyme

The procedure described in Example 2 was repeated using Sal I restriction enzyme and buffer (a high strength buffer) in place of the PST restriction enzyme and buffer. Only circular pBR322 DNA was observed in the column effluent from tube B, indicating that passage of the mixture through the column had removed all of the Sal I restriction enzyme before it could cut the DNA.

Example 5

Preparation of Rehydrated Silica Gel Using Hydrochloric and Nitric Acids

Silica gel (PSM300 Zorbax, DuPont) was first heated at 300° C. for 2 h, and then at 540° C. for 21 h in a quartz crucible in a muffle furnace. Twenty grams of this silica gel were then placed in a covered Teflon TM beaker containing 500 mL of 10% (v/v) hydrochloric acid and the mixture was heated at 100° C. for 4 h. The mixture was allowed to cool to room temperature for several hours and then filtered. The silica gel was washed with 1 L of distilled, deionized water and then transferred to a Teflon TM beaker containing 500 mL of 10% (v/v) nitric acid. The mixture was heated at 100° C. for 4 h, allowed to cool to room temperature and then filtered. The silica gel was washed with 1 L of water and then the hydrochloric and nitric acid washes were repeated. Finally, the silica gel was heated in distilled, deionized water (500 mL) for 4h at 100° C., allowed to cool to room temperature, filtered, washed with distilled, deionized water (1.5 L), rinsed with acetone (300 mL) and dried at 110° C.

A portion of this rehydrated silica gel was tested for DNA recovery as described in Example 1; 87.2% of a 1 μg sample of DNA was recovered.

Example 6

Removal of Alkaline Phosphatase from Dephosphorylation Reaction Mixtures

Linearized DNA (pBR322 DNA digested with PST restriction enzyme) was dissolved in 80 μL of dephosphorylation buffer (50 mM Tris·HCl, 1 mM EDTA, pH 8.2) and 1 μL (0.5 units) of calf intestinal alkaline phosphatase was added. The mixture was incubated at 37° C. for 30 min. A 40 μL aliquot of the reaction mixture was removed and 7.6 μL of 0.25 M HCl was added to the aliquot to adjust the pH to 6.0. The neutralized aliquot was then spun through a 40 mg column of rehydrated silica gel, prepared as in Example 2, which had previously been packed and wetted with dephosphorylation buffer (pH 6.0).

The recovered column effluent was then analyzed for active alkaline phosphatase in an enzyme assay: To the column effluent was added 10 μL of 1 M Tris·HCl (pH 8.0) to adjust the pH to 7.8. The aliquot was then added to 100 μL of assay buffer containing 0.1 M Tris HCl pH 9.5, 0.1M NaCl, 50 mM MgCl and 0.22 μg/mL BCIP, a colorless substrate for the enzyme alkaline phosphatase, which is converted by the enzyme to a colored product. The assay reaction was allowed to proceed for 2 h, and then the insoluble colored product was collected onto 2 mm diameter filters.

Control reactions which contained 0.25 units of active alkaline phosphatase yielded very strong blue colors. Dilutions of 0.0025 and 0.00025 units of alkaline phosphatase also produced blue colors. No blue precipitate was visible from the column effluent which originally contained 0 25 units prior to passing through the column, indicating that the column removed at least 99.99% of the alkaline phosphatase from the sample as it passed though the column. To insure complete removal of the enzyme, it is necessary to acidify the alkaline phosphatase dephosphorylation mixture before passing it through the column. At pH 8.2, only 99.9% of the enzyme was removed.

In a similar experiment, up to 5 units of alkaline phosphatase were removed with >99.99% efficiency using the procedure described above.

Example 7

Purification of Bacterial DNA from Whole Blood

Whole human blood collected from healthy donors was spiked with *E. coli* bacteria whose DNA contained an insert of herpes simplex virus DNA (5 μg, New England Nuclear Corp., Billerica, Mass.). The spiked blood sample (10 mL) was lysed in an Isolator TM tube (Du Pont) to disrupt the red blood cells. Intact bacteria were then isolated by spinning the Isolator TM tube in a centrifuge to form a 1.5 mL layer of bacterial sediment at the bottom of the tube and removing the supernatant. The bacteria were then lysed in 2% sodium dodecyl sulfate (SDS) for 30 min at 65° C. The bacteria from the blood sample were heated to 100° C. for 10 min to coagulate the bulk of the proteinaceous material. The coagulate was then sedimented in a centrifuge for 10 min, and the supernatant was recovered. The coagulated mass was then broken up in distilled water (1 mL) to wash any DNA from the mass, and after centrifugation, the supernatant was recovered and added to the original supernatant. This process was then repeated.

At this point, the freed bacterial DNA had been isolated in 4 mL of liquid that still contained a substantial quantity of protein (>10 mg/mL) as evidenced by the rusty red color imparted to the sample by the residual heme proteins (among others). To remove this residual protein, the sample was placed on the head of a spin column packed with rehydrated silica gel (prepared as in Example 2) that had been previously wetted with 4 mL of TE (pH 6.75) buffer. The sample was flowed into the bed of the column by low-speed centrifugation, and then the centrifuge was turned to high speed to force the DNA out of the column. After the effluent had been collected (10 min), the column was washed with 1 mL of TE (pH 6.75) buffer and the wash was added to the column effluent. The purified DNA sample was reduced to dryness under vacuum and then assayed in a standard hybridization filter assay.

12 μL each of 1M NaOH and 3M NaCl were added to the dried DNA sample dissolved in 100 mL of TE (pH 6.75) buffer. The sample was heated at 95° C. for 5 min to denature the DNA, cooled and stored on ice to prevent rehybridization.

Aliquots of the denatured sample were spotted on GeneScreen Plus TM (New England Nuclear) which had previously been assembled in a Hybridot Manifold (Bethesda Research Laboratory) and wetted with 5X SSC buffer (0.75 M NaCl, 0.075 sodium citrate, pH 7.0). The samples were slowly pulled through the filter by applying a vacuum and then the spotted samples were washed by pulling 100 μL of 3M ammonium acetate through the sample spots. The filter containing the spotted samples was removed from the manifold and prehybridized for 30 min at 50° C. in 1 mL of 0.5M sodium phosphate buffer (pH 7.0) containing 2 mg/mL sonicated salmon sperm DNA (Sigma Chemical Co., St. Louis, Mo.) and 1% (w/v) sodium dodecyl sulfate (SDS) (Sigma Chemical Co.).

A $^{32}$P-labeled pHSV106 DNA probe (200 μL, 0.15 ug, Oncor, Inc., Gaithersburg, Md.) complementary to the HSV DNA insert in the *E. coli* DNA was added to the hybridization mixture. The filter was heated at 60° C. for 30 min and washed at 60° C. with two 50 mL aliquots of 0.1M sodium phosphate buffer (pH 7.0) containing 1% (w/v) SDS to remove any nonhybridized DNA probe. The filter was air-dried at room temperature and then autoradiographed overnight with Kodak RP film.

The results of this experiment and an analogous experiment using a standard phenol extraction procedure indicate that intact, hybridizable DNA was recovered from the spin column with about the same efficiency as from a phenol extraction. Moreover, blank blood samples (i.e., not spiked with the *E. coli* DNA) which were passed through spin columns did not yield dots in the hybridization assay, indicating that the rehydrated silica gel in the spin columns did not introduce interferences or contaminants into the sample.

Recovery of DNA from Various Silica Gel Samples

The Table shows the amount of DNA recovered from nine rehydrated silica gel samples (Samples A-I), four untreated, commercially available silica gels (Samples J-N) and two rehydrated silica gels (Samples O-P) which were intentionally contaminated with various metals.

TABLE

| Silica | % DNA Recovered |
|---|---|
| A | 90.7 |
| B | 89.9 |
| C | 92.5 |
| D | 76.1 |
| E | 87.7 |
| F | 91.5 |
| G | 92.9 |
| H | 89.4 |
| I | 91.8 |
| J | 22.4 |
| K | 61.2 |
| L | 66.3 |
| M | 26.8 |
| N | 41.3 |
| O | 26.6 |

| Silica | % DNA Recovered |
|---|---|
| P | 18.4 |

Sample

A = Zorbax ™ silica (PSM2000, Du Pont) pore size 2000 Å, prepared according to Example 2A.

B = Zorbax ™ silica (PSM1000, Du Pont), pore size 1000 Å, prepared according to Example 2A.

C = Zorbax ™ silica (PSM300, Du Pont), pore size 300 Å, heated to 925° C., then prepared according to Example 2A.

D = Zorbax ™ silica (PSM300, Du Pont), pore size 300 Å, heated to 850° C., then prepared according to Example 2A.

Sample A = Zorbax ™ silica (PSM2000, Du Pont) pore size 2000 Å, prepared according to Example 2A.

B = Zorbax ™ silica (PSM1000, Du Pont), pore size 1000 Å, prepared according to Example 2A.

C = Zorbax ™ silica (PSM300, Du Pont), pore size 300 Å, heated to 925° C., then prepared according to Example 2A.

D = Zorbax ™ silica (PSM300, Du Pont), pore size 300 Å, heated to 850° C., then prepared according to Example 2A.

Sample E, F = Zorbax ™ silica (PSM300, Du Pont), pore size 300 Å, heated to 975° C., then prepared according to Example 2A.

G = 300 Å pore size silica prepared from tetraethylorthosilicate.

H, I = Fractosil ™ 500 (E. Merck), treated with $HCl/HNO_3$ as described in Example 1A.

J = Zorbax ™ silica (PSM150, Du Pont), pore size 150 Å, untreated.

K = Vydac ™ silica (lot 3700, The Sep/a/ra/tions Group, Hesperia, Calif.).

L = Fractosil ™ 500 (E. Merck), untreated.

M = Nucleosil-100-S (Machery-Nagel), West Germany), untreated.

N = Nucleosil-300 (Machery-Nagel, West Germany), untreated.

O = Sample F, intentionally contaminated with 500 ppm each of Fe, Mg and Na.

P = Sample F, intentionally contaminated with 500 ppm Al.

What is claimed is:

1. A process for separating enzymes from nucleic acids which comprises
   a. contacting a solution containing enzymes and nucleic acids with a rehydrated silica gel said rehydrated silica gel having a specific surface area of 50 to 150 $m^2/g$ and pores throughout having an effective diameter of 60 Å to 150 and having surface hydroxyl groups at a concentration of 0.1 $\mu mol/m^2$ to 8 $mol/m^2$ and at a $pK_a$ between 6 and 10 capable of binding enzymes to leave an unbound fraction containing the nucleic acids; and
   b. isolating the unbound fraction.

2. A process as in claim 1 wherein said rehydrated silica gel is a particulate material substantially devoid of trivalent metal cations on its surface and having surface hydroxyl groups at a concentration of 0.1 $\mu mol/m^2$ to 8 $\mu mol/m^2$ and at a $pK_a$ between 6 and 7.5.

3. A process as in claim 1 wherein said nucleic acids contain DNA.

4. A process as in claim 2 wherein said nucleic acids contain DNA.

* * * * *